(12) United States Patent
Gonzalez-Banos et al.

(10) Patent No.: US 8,355,804 B2
(45) Date of Patent: Jan. 15, 2013

(54) INTERFACE FOR SENSOR QUERY AND CONTROL

(75) Inventors: Hector H. Gonzalez-Banos, Mountain View, CA (US); Joel A. Wormer, San Jose, CA (US); Li Guan, Chapel Hill, NC (US)

(73) Assignee: Honda Motor Co., Ltd., Tokyo (JP)

( * ) Notice: Subject to any disclaimer, the term of this patent is extended or adjusted under 35 U.S.C. 154(b) by 568 days.

(21) Appl. No.: 11/532,492

(22) Filed: Sep. 15, 2006

(65) Prior Publication Data

US 2007/0078527 A1  Apr. 5, 2007

Related U.S. Application Data

(60) Provisional application No. 60/717,682, filed on Sep. 15, 2005.

(51) Int. Cl.
*G05B 11/01* (2006.01)
(52) U.S. Cl. ............. 700/19; 700/65; 710/1; 718/100; 711/154
(58) Field of Classification Search .......... 700/19, 700/65; 718/100; 711/154; 710/1
See application file for complete search history.

(56) References Cited

U.S. PATENT DOCUMENTS

| | | | |
|---|---|---|---|
| 5,553,269 A | 9/1996 | Nunes | |
| 5,560,022 A * | 9/1996 | Dunstan et al. | 713/300 |
| 5,790,114 A * | 8/1998 | Geaghan et al. | 715/763 |
| 6,115,654 A | 9/2000 | Eid et al. | |
| 6,256,578 B1 * | 7/2001 | Ito | 701/200 |
| 6,300,936 B1 * | 10/2001 | Braun et al. | 345/156 |
| 6,415,188 B1 | 7/2002 | Fernandez et al. | |
| 6,505,086 B1 | 1/2003 | Dodd, Jr. et al. | |
| 6,889,118 B2 * | 5/2005 | Murray et al. | 700/250 |
| 6,892,216 B2 | 5/2005 | Coburn, II et al. | |
| 6,940,403 B2 | 9/2005 | Kail, IV | |
| 7,076,336 B2 | 7/2006 | Murray, IV et al. | |
| 7,302,312 B2 | 11/2007 | Murray, IV et al. | |
| 8,060,251 B2 * | 11/2011 | Gonzalez-Banos et al. | 700/246 |
| 2002/0095224 A1 * | 7/2002 | Braun et al. | 700/44 |
| 2003/0014521 A1 * | 1/2003 | Elson et al. | 709/225 |
| 2003/0074489 A1 * | 4/2003 | Steger et al. | 710/1 |
| 2003/0122677 A1 * | 7/2003 | Kail, IV | 340/573.1 |
| 2008/0071423 A1 | 3/2008 | Murray, IV et al. | |

OTHER PUBLICATIONS

Roman et al. "A Middleware Infrastructure for Active Spaces" University of Illinois at Urbana-Champaign, pp. 1-10, 2002 IEEE.*
Hac "Wireless Sensor Network Designs" University of Hawaii at Manoa, pp. 1-410, 2003 Wiley.*

(Continued)

*Primary Examiner* — Tejal Gami
(74) *Attorney, Agent, or Firm* — Fenwick & West LLP; Mark E. Duell

(57) ABSTRACT

Systems and methods are presented that enable a higher-level software application to query and control a sensor through a generic interface. In one embodiment, a system includes a controller, and interface, and a set of sensor driver modules. The interface receives a command from the controller and sends it to the driver modules. The interface includes a client, a server, and a network. The server includes two interfaces: a client interface to communicate with the client and a driver interface to communicate with the driver modules. The server also includes two buffers: a command queue and a reply queue. The command queue stores commands received from the controller (via the client). The reply queue stores replies received from the driver modules.

19 Claims, 7 Drawing Sheets

OTHER PUBLICATIONS

Besl, P.J., and Jain R.C., "Three-dimensional object recognition" ACM Computing Surveys, vol. 17, Issue 1 (Mar. 1985), pp. 75-145.*

Wang, Y.F., Maggee, M.J., and Aggarwal, J.K., "Matching three-dimensional objects using silhouettes" IEEE Transactions on Pattern Analysis and Machine Intelligence, vol. PAMI-6, No. 4 (Jul. 1984), 513-517.*

Botts, M., et al., "OGC White Paper: OGC Sensor Web Enablement: Overview and High Level Architecture" (OGC 06-050r2; Version 2.0), 2006, [online] [Retrieved on Sep. 18, 2006] Retrieved from the Internet <URL: http://www.opengeospatial.org/pt/06-046r2>.

Botts, M., "OpenGIS Sensor Model Language (SensorML) Implementation Specification" (OGC 05-086; Version 1.0), 2005, [online] Retrieved from the Internet <URL: http://vast.nsstc.uah.edu/SensorML/OGC-05-086_SensorML_edited.doc>.

Cederberg, P. et al., "A Generic Sensor Interface in Robot Simulation and Control," Proceedings of Scandinavian Symposium on Robotics, Oct. 14-15, 1999, Oulu, Finland, pp. 221-230.

Cox, S., "Observations and Measurements" (OGC 03-022r3; Version 0.9.2), 2003, [online] Retrieved from the Internet <URL: http://www.opengeospatial.org/docs/03-022r3.pdf>.

Na, A. et al., "Sensor Observation Service" (OGC 05-088r1; Version 0.1.4), 2006, [online] Retrieved from the Internet <URL: http://portal.opengeospatial.org/files/index.php?artifact id=12846>.

Niedzwiadek, H., "Sensor Web Enablement: an update," 2004, [online] Retrieved from the Internet <URL:http://www.websim.net/05-2_Niedzwiadek_SensorWeb.pdf>.

Open Geospatial Consortium, Inc., "Sensor Web Enablement and OpenGIS SensorWeb," 2006, [online] [Retrieved on Jan. 23, 2006] Retrieved from the Internet <URL: http://www.opengeospatial.org/functional/?page=swe>.

Open Geospatial Consortium, Inc., "Sensor Web Enablement Working Group," Sep. 1, 2006, [online] [Retrieved on Sep. 18, 2006] Retrieved from the Internet <URL: http://www.opengeospatial.org/projects/groups/sensorweb>.

Reichardt, M., "Sensor Web Enablement: an OGC White Paper" (OGC 05-063), 2005, [online] Retrieved from the Internet <URL: http://portal.opengeospatial.org/files/?artifact_id=11661>.

Evolution Robotics, Inc., "ERSP 3.1: Robotic Development Platform," 2005, [Online] [Retrieved Feb. 24, 2010] Retrieved from the Internet <URL: http://www.evolution.com/products/ersp/datasheet.pdf>, 4 pages.

Karlsson, N. et al., "Core Technologies for Service Robotics," Proceedings of IEEE/RSJ International Conference on Intelligent Robots and Systems (IROS), Sep. 28-Oct. 2, 2004, Sendai, Japan, 6 pages.

Munich, M. et al., "ERSP: A Software Platform and Architecture for the Service Robotics Industry," Proceedings of IEEE/RSJ International Conference on Intelligent Robots and Systems (IROS), Aug. 2-6, 2005, Edmonton, Canada, 8 pages.

PCT International Search Report and Written Opinion, PCT/US06/36092, Mar. 19, 2008, 8 Pages.

* cited by examiner

INTERFACE FOR SENSOR QUERY AND CONTROL

CROSS-REFERENCE TO RELATED APPLICATION

This application claims priority from the following U.S. provisional patent application, which is hereby incorporated by reference: Ser. No. 60/717,682, filed on Sep. 15, 2005, entitled "SensorTalk."

BACKGROUND OF THE INVENTION

1. Field of the Invention

The present invention relates to enabling a higher-level software application to query and control a sensor through a generic interface.

2. Description of Background Art

A sensor is generally queried and controlled directly via its device driver. For example, an application uses a device driver in order to query and control a sensor. Sensor device drivers have many disadvantages. Consider a sensor that is designed to communicate with a computer via a particular input/output device, such as a portable computer (PC) card. In order for an application on the computer to query or control the sensor, the application must execute in an operating system that supports the PC card. Also, communication with a sensor driver is often limited to one device at a time, which prevents multiple devices from querying or controlling a sensor simultaneously. Finally, a sensor driver often supports a fixed set of sampling rates (e.g., rates for obtaining data from the sensor), which prevents obtaining data at other rates.

What is needed is a generic interface that enables a higher-level software application to query and control a sensor.

SUMMARY OF THE INVENTION

Systems and methods are presented that enable a higher-level software application to query and control a sensor through a generic interface. In one embodiment, a system includes a controller, an interface, and a set of sensor driver modules. The controller is used to query and control the sensor via the interface. The interface uses the sensor driver modules to directly query or control the sensor. The sensor can be either a physical entity or a virtual entity.

In one embodiment, the interface communicates with the controller using a first application programming interface (API) and with the driver modules using a second API. The interface receives a command from the controller and sends it to the driver modules. Commands include sensor commands and system commands.

In one embodiment, the interface includes a client, a server, and a network. The server includes two interfaces: a client interface to communicate with the client and a driver interface to communicate with the driver modules. The server also includes two buffers: a command queue and a reply queue. The command queue stores commands received from the controller (via the client). The reply queue stores replies received from the driver modules.

In one embodiment, the interface can operate in either of two command modes: direct and continuous. In direct mode, the client sends commands to the server in blocking mode. In continuous mode, the client sends commands to the server in non-blocking mode. In streaming mode, which is a particular type of continuous mode, one command received from a client can cause a server to periodically instruct the sensor to execute the command. In batch mode, which is another particular type of continuous mode, a server uses buffering to enable a sensor to achieve higher rates of data processing.

In one embodiment, a system includes multiple controllers. In this embodiment, the interface includes multiple clients. In another embodiment, a system includes multiple sets of driver modules. In this embodiment, the interface includes multiple servers. In yet another embodiment, a system includes multiple interfaces. In this embodiment, a first interface communicates with a composite sensor (which, in turn, includes a second interface).

BRIEF DESCRIPTION OF THE DRAWINGS

The invention is illustrated by way of example, and not by way of limitation, in the figures of the accompanying drawings in which like reference numerals refer to similar elements.

DETAILED DESCRIPTION OF THE EMBODIMENTS

Figure 1:
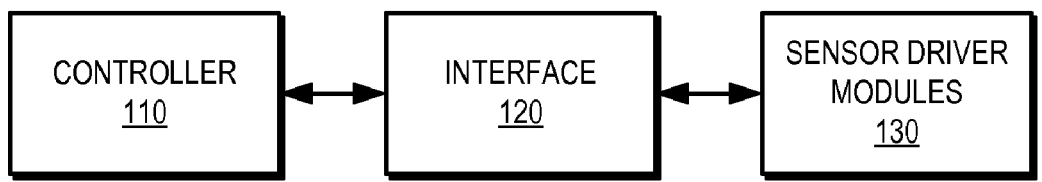
FIG. 1 illustrates a block diagram of a system for enabling a higher-level software application to query and control a sensor through a generic interface, according to one embodiment of the invention.

In the following description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Some portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

The present invention also relates to an apparatus for performing the operations herein. This apparatus is specially constructed for the required purposes, or it comprises a general-purpose computer selectively activated or reconfigured by a computer program stored in the computer. Such a computer program is stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems are used with programs in accordance with the teachings herein, or more specialized apparatus are constructed to perform the required method steps. The required structure for a variety of these systems will appear from the description below. In addition, the present invention is not described with reference to any particular programming language. It will be appreciated that a variety of programming languages may be used to implement the teachings of the invention as described herein.

1. System for Sensor Query and Control

FIG. 1 illustrates a block diagram of a system for enabling a higher-level software application to query and control a sensor through a generic interface, according to one embodiment of the invention. The system 100 includes a controller 110, an interface 120, and a set of sensor driver modules 130. The interface 120 is communicatively coupled to both the controller 110 and the set of sensor driver modules 130. The controller 110, the interface 120, and the set of sensor driver modules 130 represent groups of functionality and can be implemented in only hardware, only software, or a mixture of both. In addition, while they are illustrated as separate modules in FIG. 1, the functionality of multiple modules can be provided by a single software application or hardware device. Alternatively, the functionality of one module can be provided by multiple software applications or hardware devices.

In one embodiment, the controller 110 comprises a software application used to query and/or control a sensor. The controller 110 communicates with the sensor (not shown) via the interface 120. Signals sent from the controller 110 to the interface 120 include, for example, commands to be executed by the sensor. Signals sent from the interface 120 to the controller 110 include, for example, the sensor's replies to commands that it has received. In one embodiment, signals sent between the controller 110 and the interface 120 comply with an application programming interface (API) that is provided by the interface 120.

In one embodiment, the set of sensor driver modules 130 comprises a set of software drivers and/or libraries that can be used to directly query or control a sensor (not shown). Signals sent from the interface 120 to the set of sensor driver modules 130 include, for example, commands to be executed by the sensor. The commands sent are determined based on the commands received from the controller 110. Signals sent from the set of sensor driver modules 130 to the interface 120 include, for example, the sensor's replies to commands that it has received. In one embodiment, signals sent between the interface 120 and the set of sensor driver modules 130 comply with a second API that is provided by the set of sensor driver modules 130.

The sensor that is queried or controlled by the set of sensor driver modules 130 can be either a physical entity or a virtual (i.e., simulated) entity. Physical entities are tangible. Virtual entities can include software models that represent sensors.

The first API (between the controller 110 and the interface 120) provides a way for a controller 110 to query and control a sensor. The API includes both commands (which are sent from the controller 110 to the interface 120) and replies (which are sent from the interface 120 to the controller 110). In one embodiment, the API is independent of both the hardware and software of the controller 110. Thus, the API can be used with many different controllers 110.

In one embodiment, a sensor's state (which includes its configuration and/or data that it has sensed) is represented by one or parameters. One exemplary parameter of a sensor is what type of data it reports (e.g., image data, force data, sound data, and temperature data). Another exemplary parameter is how often the sensor senses data (i.e., its sampling rate or "fundamental frequency"). Yet another exemplary parameter is the format in which the sensor reports data. For example, a temperature sensor could report temperature in degrees Fahrenheit, degrees Celsius, or degrees Kelvin. An image sensor could report data as a bitmap file (.bmp), a JPEG file (.jpg), or a GIF file (.gif).

A particular parameter may or may not be configurable by a user. For example, the type of data reported by a sensor is usually built in to the sensor and cannot be changed. As another example, the format in which the sensor reports data is usually not built in to the sensor and can be changed. Note that while the actual data reported by the sensor might be configurable, setting this data could defeat the purpose of sensing the data in the first place.

In one embodiment, the first API includes a system portion and a sensor portion. The system portion of the API is sensor-independent. This means that the system portion is compatible across various sensors at both a software and hardware level. In one embodiment, the system portion comprises various commands and replies regarding system status. The commands include, for example, setTransmissionMode (e.g., direct or continuous), getDescription (described below), setPeriodicPublishing (described below), subscribe, and release. The replies include, for example, status signals and error signals, such as current transmission mode, client identifier, failed subscription, and failed release. In one embodiment, all system commands are the same length. In another embodiment, all system replies are the same length.

The sensor portion of the API is sensor-dependent. This means that the sensor portion can change based on which sensor is being used. For example, the commands that a sensor can execute and the replies that a sensor can generate can differ based on which sensor is being used.

In one embodiment, the sensor portion of the API generally comprises a set of rudimentary commands over the sensor's parameters. These commands can theoretically be used in conjunction with any parameter of any sensor. In one embodiment, the commands include Read, Set, SetDefault, Reset, SetFactoryDefault, FactoryReset, Lock, and Unlock. The Read command queries and returns the current value of a parameter. The Set command sets the value of a parameter to a specified value (if the parameter's value can be modified). The SetDefault command sets a parameter's default value. The Reset command sets the value of a parameter to its default value. The SetFactoryDefault command sets a parameter's factory default value. The FactoryReset command sets the value of a parameter to its factory default value. The Lock command prevents the value of a parameter from being changed. The Unlock command allows the value of a parameter to be changed. In one embodiment, each of these rudimentary commands generates a rudimentary reply when the command is executed by a sensor.

The specific commands available in the sensor portion of the API differ based on the sensor that is being used. In one embodiment, the sensor portion of the API assigns these specific commands to the rudimentary commands provided by the system. For example, if a force plate sensor is being used, the sensor portion of the API might include the commands SetShearForceSensitivity and ReadShearForceSensitivity. SetShearForceSensitivity might be a specific implementation of the rudimentary command Set, while ReadShearForceSensitivity might be a specific implementation of the rudimentary command Read. In one embodiment, a sensor registers each of its parameters with the system, and the system assigns each parameter a unique identifier. This unique identifier is then used in conjunction with a rudimentary command in order to customize the rudimentary command to affect that particular parameter. In one embodiment, sensor commands can vary in length. In another embodiment, sensor replies can vary in length.

In one embodiment, the specific replies generated in the sensor portion of the API differ based on the sensor that is being used. In one embodiment, the sensor portion of the API assigns these specific replies to the rudimentary replies provided by the system.

In one embodiment, specific information about a sensor's capabilities is present in the first API (e.g., based on which sensor commands and sensor replies are supported by the API). Since differences between sensors can affect the overall API, they can also affect the controller 110. In one embodiment, there exists a machine-readable description of a sensor and its parameters. In this embodiment, a controller 110 can parse the description to learn about the sensor portion of the first API. In this way, the controller 110 can determine which features are available from the sensor and how to invoke them. In one embodiment, the description includes one or more characteristics for each parameter, such as the parameter's name, whether it can be changed/configured, its units of measure, its default value, its factory default value, and its range of possible values. In one embodiment, the controller 110 obtains the machine-readable description by using the command getDescription, which obtains the description from the set of sensor driver modules 130.

In one embodiment, the controller 110 sends a command (or set of commands) to the interface 120 in blocking mode. In this embodiment, the controller 110 waits to receive a reply signal (or multiple reply signals, one for each command) from the interface 120 before it issues the next command (or set of commands). In other words, after the controller 110 has sent a command (or set of commands) to the interface 120, the controller's execution stops and resumes only when the controller receives an acknowledgement (or multiple acknowledgements, one for each command) from the interface 120. In particular, the controller 110 does not send a new command (or set of commands) to the interface 120 until it has received an acknowledgment regarding the previous command (or multiple acknowledgements regarding the previous commands). This acknowledgement can indicate, for example, that the interface 120 has received the command(s), that the interface 120 has successfully begun executing the command (s), or that the interface 120 has finished executing the command(s). Thus, we have the following series of events: The controller 110 issues a command (or set of commands) to the interface 120; the controller 110 receives an acknowledgement (or multiple acknowledgements, one for each command) from the interface 120; and only then does the controller 110 issue a second command (or set of commands) to the interface 120.

In another embodiment, the controller 110 sends a command (or set of commands) to the interface 120 in non-blocking mode. In this embodiment, after the controller 110 has sent a command (or set of commands) to the interface 120, the controller's execution continues even though it has not received an acknowledgement (or multiple acknowledgements, one for each command) from the interface 120.

In one embodiment, the interface 120 executes a received command as soon as possible. In another embodiment, a command includes a starting time that indicates when the command should be executed. In one embodiment, a starting time is absolute, such as 13:10:30, which represents 1:10 pm and 30 seconds. In another embodiment, a starting time is relative and reflects the reverse priority of the command. For example, a first command with a starting time of 40 will be executed after a second command with a starting time of 20, even if the first command was received before the second command.

In one embodiment, the starting time represents the number of seconds or milliseconds to wait until executing the command. If the starting time is zero or negative (or not provided), then the command is executed as soon as possible. In one embodiment, commands with the same priority are executed in their arrival order. In one embodiment, the starting time is provided as an argument to the command.

Sensor Commands—As described above, a sensor command is used to determine or modify a sensor's state, such as its configuration or sensed data. Different types of sensors can have different types of parameters, each of which may or may not be configurable. In one embodiment, the Read command specifies one or more variables (e.g., sensor parameters) for which status information should be returned. In another embodiment, the Read command returns the entire set of sensor status information (e.g., for all sensor parameters and for the sensed data).

System Commands—As described above, a system command is used to query or control system status. In one embodiment, system status includes communication mode. Communication mode, which can be either direct or continuous, is described below.

2. Interface for Sensor Query and Control

Figure 2:
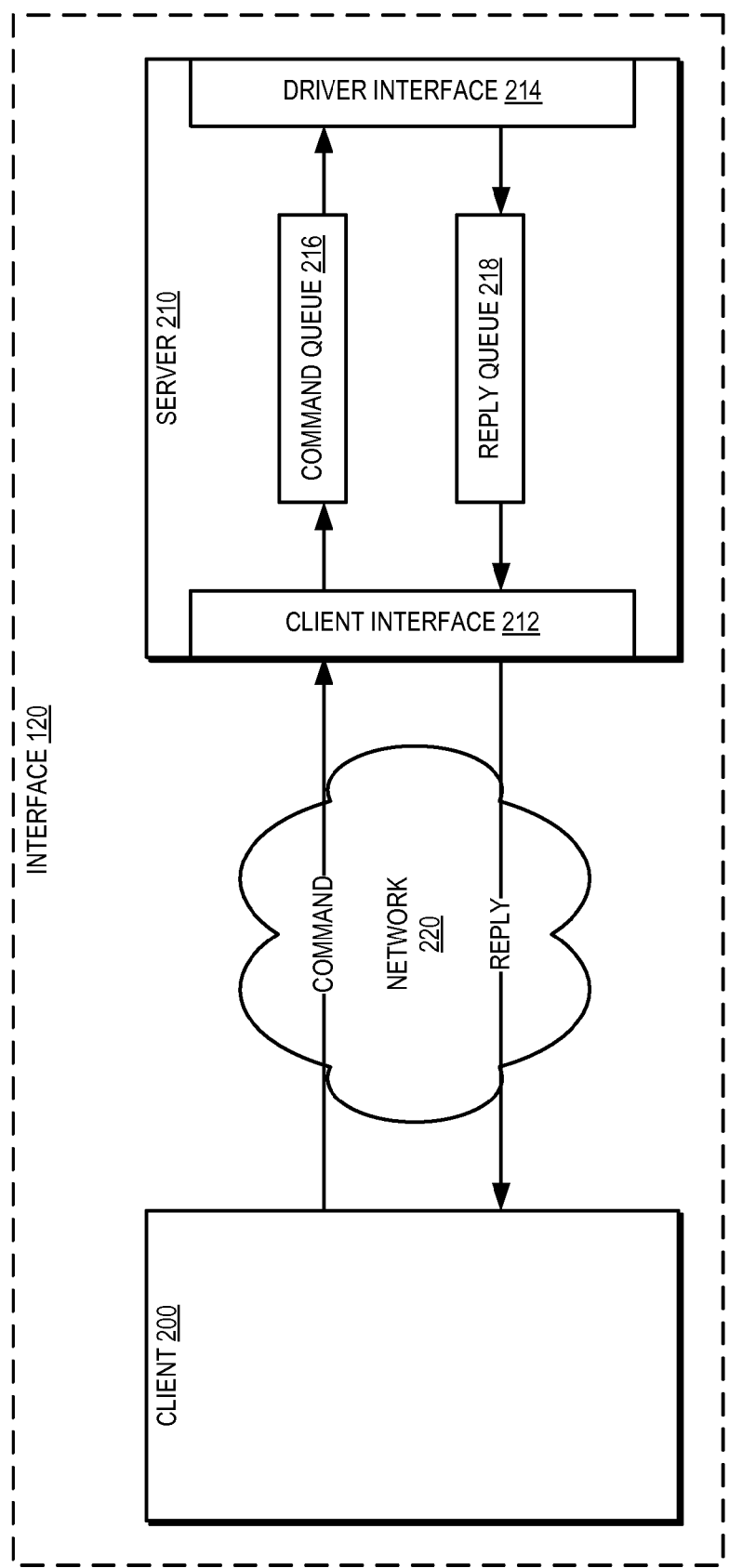
FIG. 2 illustrates a more detailed view of the interface shown in FIG. 1, according to one embodiment of the invention.

FIG. 2 illustrates a more detailed view of the interface shown in FIG. 1, according to one embodiment of the invention. The interface 120 includes a client 200, a server 210, and a network 220. The client 200 is communicatively coupled to the server 210 via the network 220. The client 200 and the server 210 represent groups of functionality and can be implemented in only hardware, only software, or a mixture of both. In addition, while they are illustrated as separate modules in FIG. 2, the functionality of multiple modules can be implemented in a single software application or hardware device.

In one embodiment, the client 200 and the server 210 comprise software applications running on top of operating systems. Any programming or scripting language can be used to write the software applications, such as C++, Java, and Perl. Any operating system can be used, such as Linux, Mac OS from Apple Computer, Inc. of Cupertino, Calif., and Windows from Microsoft Corp. of Redmond, Wash. In one embodiment, the client 200 and the server 210 use different programming languages, different software applications, and/or different operating systems. In order to preserve compatibility across operating systems, in one embodiment, the client 200 and/or the server 210 are implemented using software libraries that can be ported to various hardware and software platforms. In particular, proprietary software tools and libraries are not used.

In one example, a sensor is a force plate, such as the Type 9286AA force plate sold by Kistler Instrument Corporation of Amherst, N.Y. An exemplary sensor driver 130 is defined by deriving from an abstract base class HSensorTalkDriver. The driver 130 implements its functionality in the form of functions (either free functions or class methods) that perform operations on parameters that represent the state of the sensor. The Appendix includes a description of the sensor's parameters.

The operations (commands) supported by the driver are registered, and other initialization is performed, by overriding the HSensorTalkDriver::Start( ) method. In one embodiment, the initialization sequence is as follows: 1) Registration of parameters. 2) Registration of parameter operation methods (commands). 3) Initialization of the sensor. 4) Other driver initialization (e.g., starting a sampling thread).

The server 210 includes two interfaces (a client interface 212 and a driver interface 214) and two buffers (a command queue 216 and a reply queue 218). The client interface 212 enables the server 210 to receive signals from and send signals to the client 200 via the network 220. The driver interface 214 enables the server 200 to receive signals from and send signals to the set of sensor driver modules 130.

In one embodiment, described below but not shown here, the client 200 includes one buffer (a reply cache).

The network 220 comprises any type of communication mechanism. If the client 200 and the server 210 are co-located (e.g., software applications running on the same machine), the network 220 can include local communication mechanisms such as shared memory. If the client 200 and server 210 are not co-located, the network 220 can include remote communication mechanisms such as communications protocols running on top of wired or wireless connections. The communications protocols can include, for example, the Transmission Control Protocol/Internet Protocol (TCP/IP) suite, the User Datagram Protocol (UDP), or the Data Distribution Service for Real-time Systems Specification from Object Management Group, Inc. of Needham, Mass.

The communication mechanism, regardless of its type, supports a communication protocol. The communication protocol supports four command modes, which will be described below. In one embodiment, the communication protocol is based on network packages, each of which includes a header portion and a payload portion. In this embodiment, the client 200 and server 210 communicate by sending packages to each other via the network 200.

In a package sent from the server 210 to the client 200, the payload portion includes one or more replies, where a reply is either a status signal or an error signal. In one embodiment, each time a reply is placed in the reply queue 218, the server 210 creates a package containing that reply and sends the package to the client 200 via the client interface 212. In another embodiment, the server 210 creates and sends packages periodically, for example after a particular period of time has elapsed (if any replies have been placed in the reply queue 218) or after a particular number of replies have been placed in the reply queue 218.

In a package sent from the client 200 to the server 210, the payload portion includes one or more commands. The header portion is of a fixed-length and includes the size of the payload.

The data in a package can be of any format, such as binary, plain text (e.g., XML), etc. In one embodiment, the data is plain text that is parsed by the client 200 and the server 210. In another embodiment, the data is in binary format, and the client 200 and the server 210 convert values within a payload to integers, floats, chars (characters), and/or other integral types. In yet another embodiment, values within a payload are stored in network-byte-order format to address byte ordering differences among little-endian and big-endian processors.

The network 220 has various characteristics, such as latency and bandwidth, that will vary based on the communication mechanisms used. For example, the network's latency will probably increase as the distance between the client 200 and the server 210 increases. Since the interface 110 is a black box from the controller's perspective, the controller 110 works the same way regardless of the connection characteristics. This modularity is achieved by operating the interface 110 in various communication modes, which will be explained below. Thus, the network 220 is versatile enough to enable both remote and local sensor query and control.

Returning to the server 210, the client interface 212 reads packages received from the client 200. The one or more commands in each package payload are parsed. Then, the commands are executed by the driver interface 214 by sending signals to the sensor driver modules 130.

The commands are not necessarily executed in the order that they arrived. Instead, they are stored in a command queue 216 and scheduled for execution according to their starting times, as described above.

If a sensor generates a reply signal in response to a command, the reply signal is transmitted to the driver interface 214 via the set of sensor driver modules 130. The reply signals are sent by the client interface 212 to the client 200. The replies are not necessarily sent to the client 200 in the order that they arrived. Instead, they are stored in a reply queue 218. In one embodiment, the replies in the reply queue 218 are scheduled for transmission according to their insertion times into the queue.

3. Communication Mode

Figure 3:
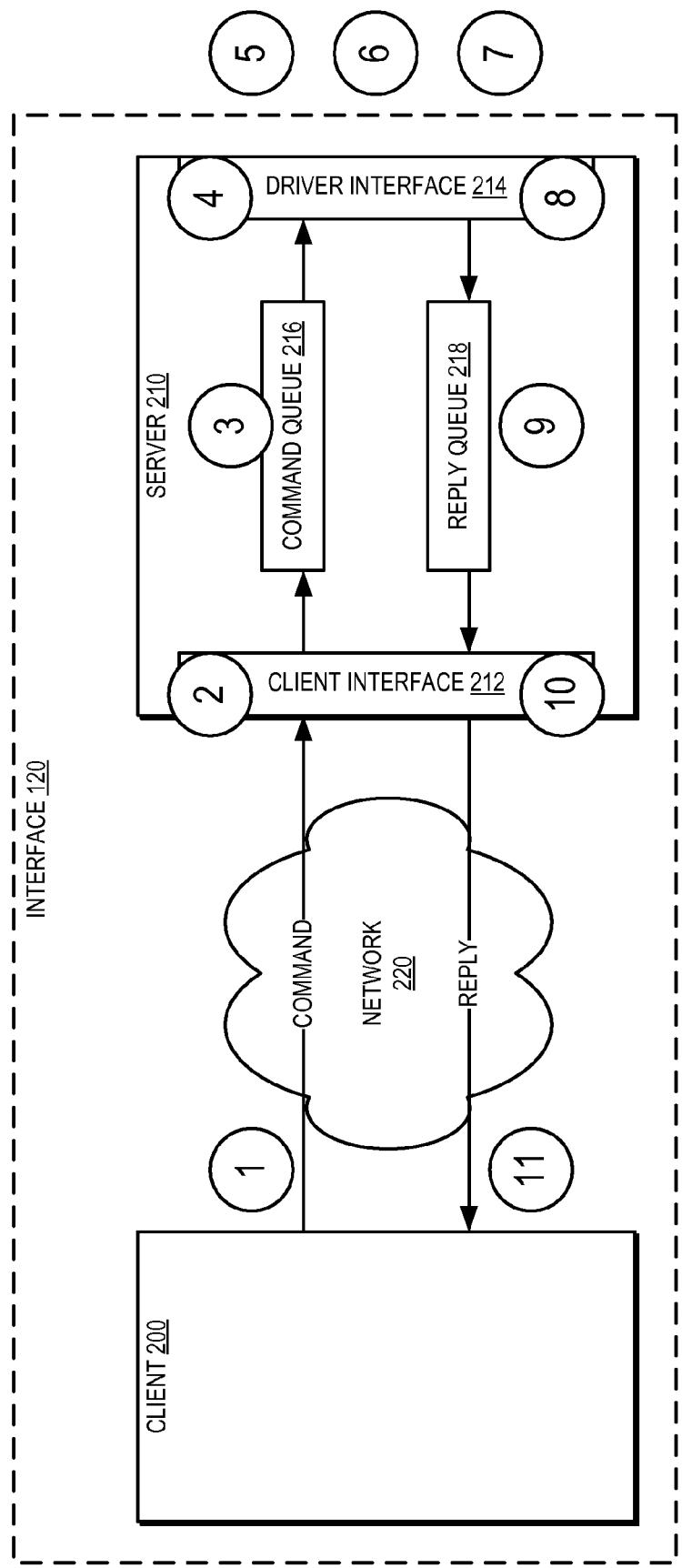
FIG. 3 illustrates a how a signal flows through the elements shown in FIG. 2, according to one embodiment of the invention.

The interface 110 can operate in either of two communication modes: direct or continuous. Before these modes are described, consider how a signal generally flows through the interface 110. FIG. 3 illustrates a how a signal flows through the elements shown in FIG. 2, according to one embodiment of the invention. FIG. 3 illustrates the following steps: 1) The client 200 sends a package (containing a set of one or more commands) to the server 210 via the network 220. 2) The client interface 212 receives the commands. 3) The commands are placed in the command queue 216. 4) The driver interface 214 accesses a command from the command queue 216. 5) The driver interface 214 sends a signal to the set of sensor driver modules 130. 6) The sensor driver modules 130 cause the sensor to execute the command. 7) The sensor generates a reply signal, which is sent to the driver modules 130. 8) The driver interface 214 receives the reply signal from the driver modules 130. 9) The reply signal is placed in the reply queue 218. 10) The client interface 212 accesses the reply signal from the reply queue 218. 11) The client interface 212 sends the reply signal to the client 200 via the network 220.

In direct mode, the client 200 sends packages to the server 210 in blocking mode. In other words, after the client 200 has sent a package to the server 210 containing a set of one or more commands (step 1), the client's execution stops and resumes only when the client receives acknowledgements from the server 210 for all of the commands in the package (sent in step 11). In particular, the client 200 does not send a new package to the server 210 until it has received acknowledgments regarding all of the commands in the previous package. An acknowledgement can indicate, for example, that the server 210 has received the command, that the server 210 has successfully begun executing the command, or that the server 210 has finished executing the command. Thus, we have the following series of events: The client 200 issues a first set of one or more commands to the server 210; the client 200 receives acknowledgements from the server 210 regarding all of the commands in the first set; and only then does the client 200 issue a second set of commands to the server 210. Note that, in direct mode, if the network 220 is slow (during step 1, step 11, or both), this will increase the amount of time between each command set issuance by the client 200.

In one embodiment, in direct mode, once a connection has been established between the client 200 and the server 210, the client 200 and the server 210 synchronize their clocks. Then, the client 200 starts accepting signals (e.g., API function calls) from the controller 110 to query or control the sensor. When an API function call is received, the client 200 creates a network package that includes one or more commands to be executed by the sensor. Each command is tagged with a unique identifier, and the package is sent to the server 210 via the network 220. The client's execution halts inside the API function call until the client 200 receives, from the server 210, acknowledgements regarding all of the commands in the sent package. In one embodiment, a time-out mechanism is present so that an API function call can return even if the server 210 crashes or the network 220 breaks down.

The server 210 receives the network package from the client 200. The client interface 212 parses the package payload and places the one or more commands into the command queue 216. Commands with starting times of zero or a negative number will be executed before commands with positive starting times, as described above. Thus, in direct mode, the transmission and execution of these types of commands follows a hand-shake model.

In direct mode, if the client's clock and the server's clock have been synchronized, the server 210 generally executes the command when its clock is equal to the command's starting time. However, if the clocks have not been synchronized, the server does not execute the command at this time. Instead, the server determines the time offset between its clock and the client's clock and executes the command when its clock is equal to the sum of the time offset and the command's starting time.

Sometimes the server 210 can fall behind in executing commands. In one embodiment, the server 210 does not execute a particular command, even if the server's clock has reached the appropriate time, unless commands that were supposed to precede the particular command have already been executed. For example, the driver interface 214 verifies that the starting time of the command with the highest priority has passed with respect to the server clock.

In continuous mode, the client 200 sends packages to the server 210 in non-blocking mode. In other words, after the client 200 has sent a package to the server 210, the client's execution continues even though it has not received an acknowledgement from the server 210.

In blocking mode, the client 200 waits to receive the one or more reply signals (sent in step 11) before it issues the next command or set of commands. Thus, replies to all the commands in one package will arrive at the client 200 prior to replies to commands in a subsequent package. In other words, if the client 200 issues a first package with a single command and then (after receiving a reply) a second package with a new command, it will always receive the reply to the first command before receiving the reply to the second command. In non-blocking mode, the client 200 does not wait to receive the reply signal before it issues the next command. Thus, replies will not necessarily arrive at the client 200 in the same order that the associated commands were issued. In other words, if the client 200 issues a first command and then a second command, it might receive a reply to the second command and then a reply to the first command.

There can be many reasons why the replies arrive in a different order. One reason is that the commands might have different priorities, so that they are executed in a different order by the server 210 (specifically, the driver interface 214). Another reason is that the commands might require different amounts of time in order to generate a reply.

In one embodiment, in order to handle replies received "out-of-order," the client 200 includes a reply cache (not shown) that stores replies received from the server 210. The reply cache can include, for example, a dictionary data structure or a binary search tree (such as a red-black tree). For a dictionary, the element keys are the original commands for which the server 210 generated a reply. In one embodiment, an element key is the unique identifier that was tagged to the command by the client 200. The client 200 can periodically query the reply cache to determine whether the reply to a particular command has been received. In one embodiment, the dictionary data structure is implemented as a hash map, such as the hash multi-map described in the C++ Standard Template Library (part of the C++ Standard Library, a standard managed by the International Organization for Standardization (ISO) and the International Electrotechnical Commission (IEC)).

In streaming mode, which is a particular type of continuous mode, one command received from a client 200 can cause a server 210 to periodically instruct the set of sensor driver modules to re-execute the same command (e.g., via the setPeriodicPublishing operation). In one embodiment, the server accomplishes this via a specialized query command that is re-inserted into the command queue 216 after it has been removed (in order to be read and executed). For example, a client 200 transmits, in streaming mode, a query command for a sensor's output (i.e., sensed data) and an associated publishing rate. The publishing rate specifies how often the server 210 should instruct the set of sensor driver modules (via the driver interface 214) to execute the query command. The server 210 inserts into the command queue 216 a query command regarding the sensor's data. After the server has removed the query command from the queue (in order to read it and instruct the set of sensor driver modules), a copy of the query command is created and reinserted into the command queue 216 with a priority that has been increased by an amount inversely proportional to the publishing rate. Thus, the query command regenerates itself for future execution by the driver interface 214. The regeneration process stops once the server 210 has received a client request to cancel the streaming.

Recall that one exemplary parameter of a sensor is how often the sensor senses data (e.g., once per second or after every 10 samples; called a "fundamental frequency"). Although a sensor might support multiple fundamental frequencies, some of the higher frequencies might be possible only if the sensor processes data off-line. In one embodiment, the server 210 signals the sensor driver module 130 to use buffering to enable a higher fundamental frequency for a sensor that has limited data processing capabilities or low-bandwidth communication to the server 210. In this embodiment, called batch mode, a sensor generates data at a high frequency, but the data is first stored in a local memory (the "batch"). This data is then read by the server 210 and transmitted to the client 200 according to the desired publishing rate.

Batch mode, which is another particular type of continuous mode, will also be described below in conjunction with composite sensors.

4. Additional Embodiments

Figure 4:
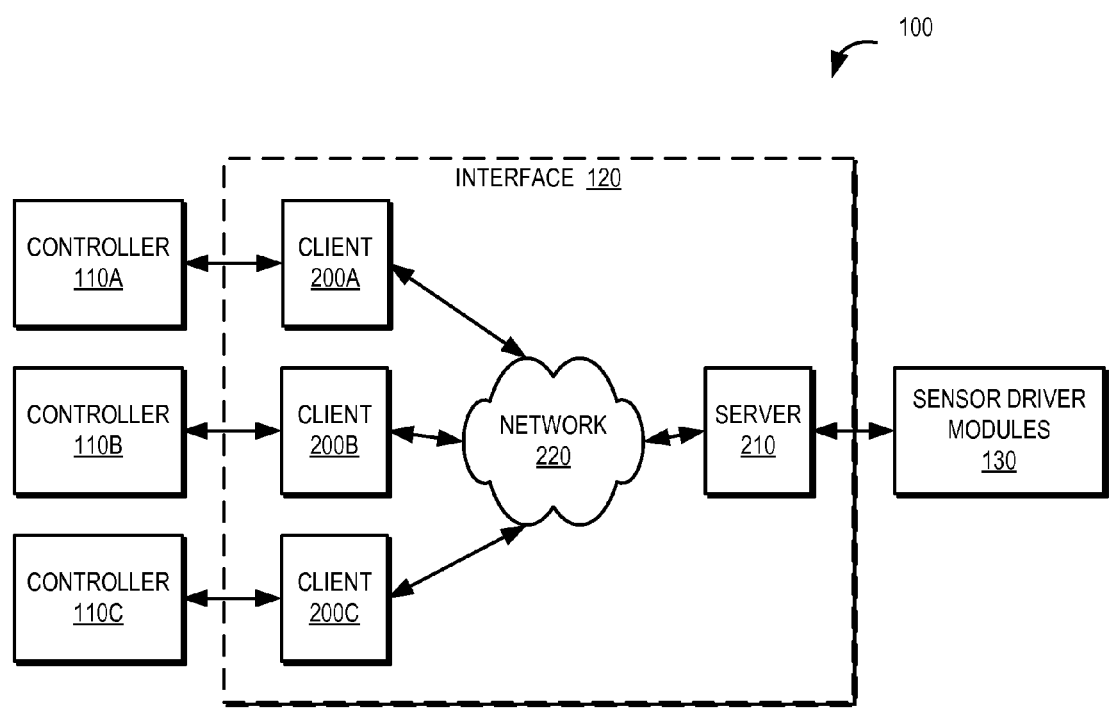
FIG. 4 illustrates a block diagram of a system for enabling multiple higher-level software applications to query and control a sensor through a generic interface, according to one embodiment of the invention.

Multiple controllers—The interface 120 described above with respect to FIG. 1 can also be used in a system where multiple controllers 110 query and/or control one sensor. FIG. 4 illustrates a block diagram of a system for enabling multiple higher-level software applications to query and control a sensor through a generic interface, according to one embodiment of the invention. The system 100 includes three controllers 110A, 110B, 110C, an interface 120, and a set of sensor driver modules 130. The system 100 in FIG. 4 is similar to the system 100 in FIG. 1, except that the system 100 in FIG. 4 includes multiple controllers 110 instead of just one. Although the illustrated embodiment shows three controllers 110, any number of controllers 110 can be used.

The controllers 110A, 110B, 110C in FIG. 4 are similar to the controller 110 in FIG. 1. In one embodiment, a controller 110 is a software application used to query and control a sensor. In one embodiment, each controller 110 runs on a different piece of hardware. In another embodiment, multiple controllers 110 run on the same piece of hardware.

The interface 120 in FIG. 4 includes three clients 200A, 200B, 200C, a server 210, and a network 220. The interface 120 in FIG. 4 is similar to the interface 120 in FIG. 1 except that the interface 120 in FIG. 4 includes three clients 200 instead of just one. Although the illustrated embodiment shows three clients 200, any number of clients 200 can be used. In one embodiment, the number of clients 200 in the interface 120 is equal to the number of controllers 110 in the system 100.

The set of sensor driver modules 130 in FIG. 4 is similar to the set of sensor driver modules 130 in FIG. 1.

When a system 100 includes multiple controllers 110, the controllers 110 can potentially interfere with each other's operation. For example, one controller 110A can issue a control command to the sensor to sample data at one rate, while another controller 110B can simultaneously issue a control command to the sensor to sample data at a different rate. In one embodiment, in order to prevent interference between controllers 110, a locking mechanism is used to control access to a sensor by various controllers 110.

Note that, in general, interference occurs only when multiple controllers 110 are issuing control commands that seek to simultaneously affect the same sensor (and sensor parameter). As discussed above, control commands can change a sensor's state and include sensor commands and system commands that set system status, while query commands cannot change a sensor's state and include sensor commands and system commands that query system status. Interference generally does not occur when 1) the commands are query commands, 2) the commands do not seek to affect the sensor simultaneously, or 3) the commands do not seek to affect the same sensor (or sensor parameter).

Figure 5:
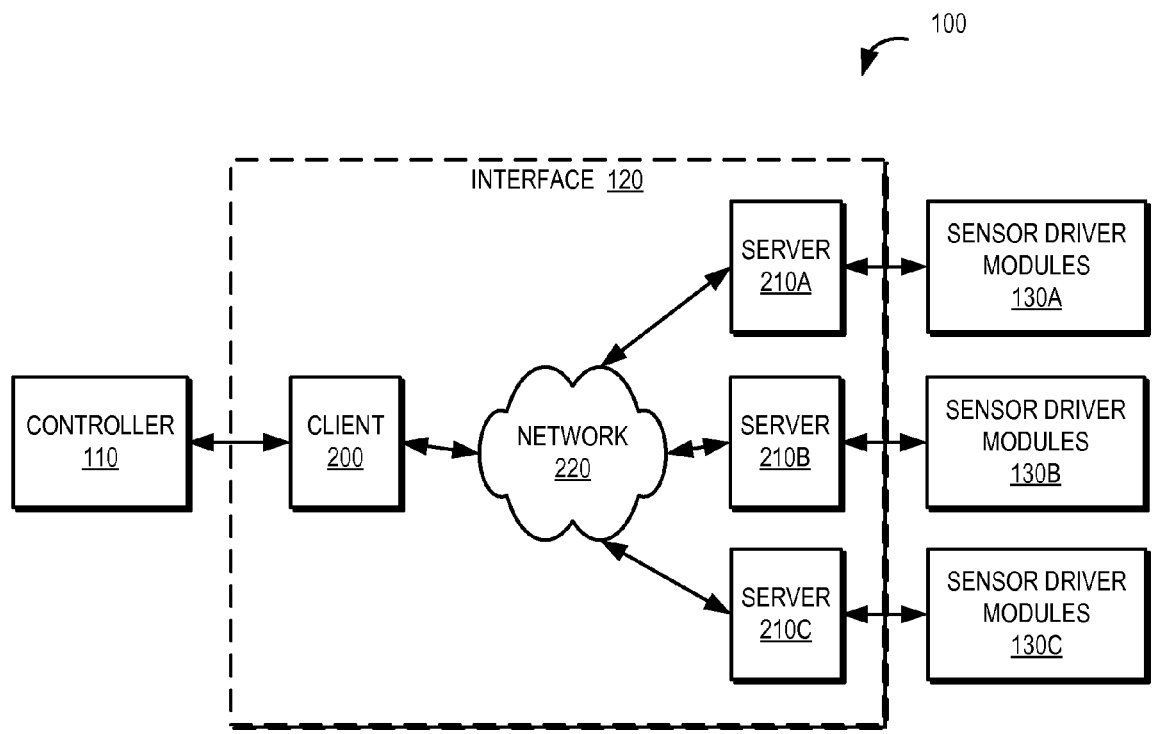
FIG. 5 illustrates a block diagram of a system for enabling a higher-level software application to query and control multiple sets of sensor drivers through a generic interface, according to one embodiment of the invention.

Multiple sets of drivers—The interface 120 described above with respect to FIG. 1 can also be used in a system where one controller 110 queries and/or controls multiple sets of sensor drivers 130. FIG. 5 illustrates a block diagram of a system for enabling a higher-level software application to query and control multiple sets of sensor drivers through a generic interface, according to one embodiment of the invention. The system 100 includes a controller 110, an interface 120, and three sets of sensor driver modules 130A, 130B, 130C. The system 100 in FIG. 5 is similar to the system 100 in FIG. 1, except that the system 100 in FIG. 5 includes multiple sets of sensor driver modules 130 instead of just one. Although the illustrated embodiment shows three sets of sensor driver modules 130, any number of sets of sensor driver modules 130 can be used.

The illustrated embodiment can be used, for example, to query and/or control a modular sensor. A modular sensor is a sensor that is made of other sensors. One example of a modular sensor is a device that can sense both temperature and humidity. Another example is a device that includes two image sensors (such as cameras). This second example will be discussed further below.

The controller 110 in FIG. 5 is similar to the controller 110 in FIG. 1.

The interface 120 in FIG. 5 includes one client 200, three servers 210A, 210B, 210C, and a network 220. The interface 120 in FIG. 5 is similar to the interface 120 in FIG. 1 except that the interface 120 in FIG. 5 includes three servers 210 instead of just one. Although the illustrated embodiment shows three servers 210, any number of servers 210 can be used. In one embodiment, the number of servers 210 in the interface 120 is equal to the number of sets of sensor driver modules 130 in the system 100.

The sets of sensor driver modules 130 in FIG. 5 are similar to the set of sensor driver modules 130 in FIG. 1. In one embodiment, each set of sensor driver modules 130 in FIG. 5 is configured to query and/or control a different sensor (or a different sensor of a modular sensor). For example, one set of sensor driver modules 130 queries or controls an image sensor, while another set of sensor driver modules 130 queries or controls a force sensor.

Note that the functionalities of a modular sensor can be greater than the sum of its parts. That is, a modular sensor can have additional functionalities above and beyond the functionalities of each of its component sensors. For example, consider a modular sensor that includes two image sensors, each of which can generate a two-dimensional (2D) image. Individually, each image sensor can generate a 2D image of a scene. Together, however, they can generate a stereo image of the scene (assuming, of course, that they are pointed in the same direction). Specifically, the outputs of the two 2D sensors can be combined to generate a stereo image. Another example of a modular sensor includes one image sensor that can generate a two-dimensional (2D) image and one image sensor that can determine depth.

In order to use the system 100 of FIG. 5 to obtain a stereo image or other composite data, the controller 110 needs to coordinate the multiple sets of sensor driver modules 130. The controller 110 might also need to perform some calculations using data obtained from the sensors. The interface 120 described above with respect to FIG. 1 can also be used to create a "composite" sensor that hides this complexity from the controller by simulating the existence of a single sensor that generates the composite data.

Figure 6:
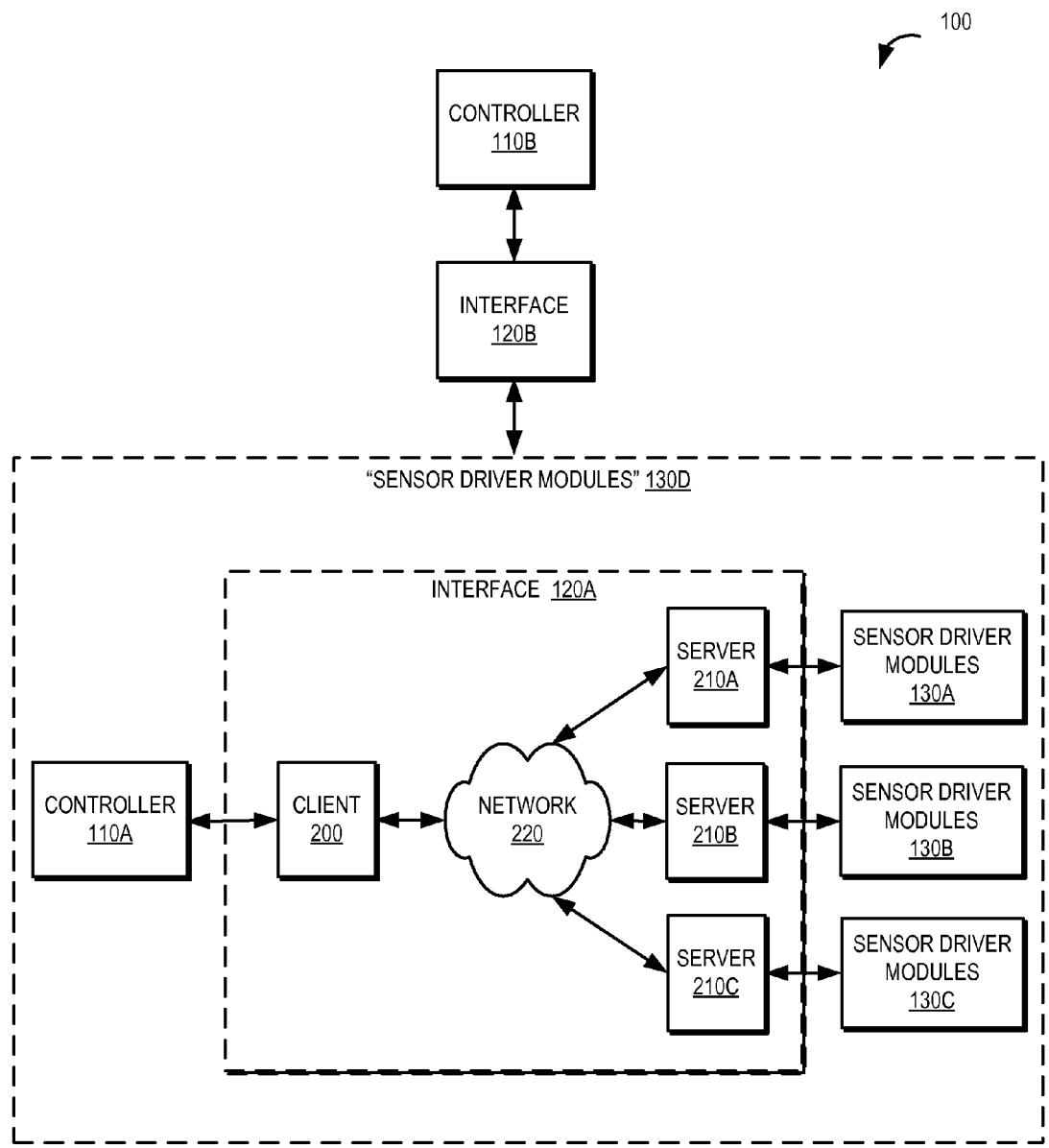
FIG. 6 illustrates a block diagram of a system for enabling a higher-level software application to query and control a composite sensor through a generic interface, according to one embodiment of the invention.

FIG. 6 illustrates a block diagram of a system for enabling a higher-level software application to query and control a composite sensor through a generic interface, according to one embodiment of the invention. The system 100 includes a controller 110B, an interface 120B, and a set of sensor driver modules 130D. Note that the set of "sensor driver modules" 130D is equivalent to the system 100 in FIG. 5. The API of the interface 120B enables the controller 110B to issue commands for composite sensor data while shielding the controller 110B from the complexity of the multiple sets of sensor modules 130A, 130B, 130C. In this way, one controller 120B can issue a command for composite data, and the other controller 120A can generate the composite data by using the multiple sets of driver modules 130A, 130B, 130C and possibly performing additional computation. In this embodiment, the controller 110B queries and controls the composite sensor via the interface 120B and the set of "sensor driver modules" 130D.

One example of a composite sensor includes multiple image sensors, each of which generates a 2D image. The composite sensor uses the 2D images to determine the visual hull of an object and makes this data available as "sensor data." A visual hull of an object is the largest volume in which the object can reside that produces the same silhouette as the object itself for all views outside the object. An image sensor's view of an object is a silhouette that sweeps out a cone in three-dimensional space. The visual hull of the object is the intersection of several silhouette cones of the object. The silhouette cones represent different views of the object as seen from different locations. The visual hull of an object is guaranteed, by definition, to fully enclose the object.

Techniques for generating visual hulls include volume intersection and shape-from-silhouette. In one embodiment, for each 2D image, one silhouette image is determined. Any of several methods can be used to determine the silhouette image, such as background subtraction, motion detection, and use of depth information. Silhouette cones are determined based on the silhouette images. The intersection of the silhouette cones represents the visual hull. Visual hulls and methods of generating them are known to those of ordinary skill in the art and are further described in "The Visual Hull Concept for Silhouette-Based Image Understanding" by A. Laurentini, IEEE Transactions on Pattern Analysis and Machine Intelligence, 16:2, February 1994, which is hereby incorporated by reference.

A composite sensor "consumes" data produced by the sensors that it contains. Ideally, the composite sensor and the contained sensors would have the same fundamental frequency (rate of data throughput). For example, a visual hull sensor would have the same fundamental frequency as the image sensors that it contains. Unfortunately, the fundamental frequency of a composite sensor is almost always lower than the fundamental frequency of a sensor within the composite sensor due to computation delay.

Note that the visual hull composite sensor described above performs various computations. For example, the composite sensor determines a silhouette image for each 2D image generated by an image sensor. The composite sensor also determines silhouette cones based on the silhouette images and intersects these cones to determine the visual hull. This computation, especially the cone intersection, can take a significant amount of time. Although each image sensor within a visual hull composite sensor might be able to generate 100 2D images per second (100 Hz), the fundamental frequency of the composite sensor might be only 10 visual hulls per second (10 Hz).

In one embodiment, batch mode is used to implement a higher fundamental frequency for a composite sensor with limited data processing capabilities. For example, a sensor within the composite sensor generates data at its fundamental frequency. This data is used by the internal controller 110A to perform various calculations and generate composite data at the composite sensor's fundamental frequency, which will be lower than the internal sensor's fundamental frequency if the composite sensor's data processing capabilities are limited.

In batch mode, the external interface 120B signals the set of sensor driver modules 130D to process a data batch. In one embodiment, the internal controller 110A buffers the data from the internal sensors before it uses this data to generate composite data. Once the batch of composite data has been generated, it is transmitted to the external interface 120B at the desired publishing rate, which is higher than the composite sensor's fundamental frequency under continuous mode operation. For example, the desired publishing rate can be equal to the internal sensor's fundamental frequency. Thus, in batch mode, there is a time delay between when a sensor within a composite sensor reports its data and when the composite sensor reports its composite data. However, the external controller 110B will see a data rate equal to the internal sensor's fundamental frequency, rather than the slower composite sensor's rate.

Recall that a composite sensor hides complexity from a controller by simulating the existence of a single sensor that generates composite data. The composite sensors described above used multiple sensors. A different type of composite sensor uses a sensor and a motor. For example, consider a telescope, which is a sensor with various capabilities. If the telescope is connected to a base that can be mechanically-positioned, the telescope can be moved by issuing commands to its mechanical base, which gives the telescope additional capabilities. In one embodiment, a composite sensor is used to represent the telescope with its additional capabilities enabled the by movable base. Another example of a composite sensor is a document camera (e.g., a camera located above a table that points downwards at the table in order to capture documents on the table) that is connected to a base that can be mechanically-positioned in order to view different areas of a table and documents located therein.

Figure 7:
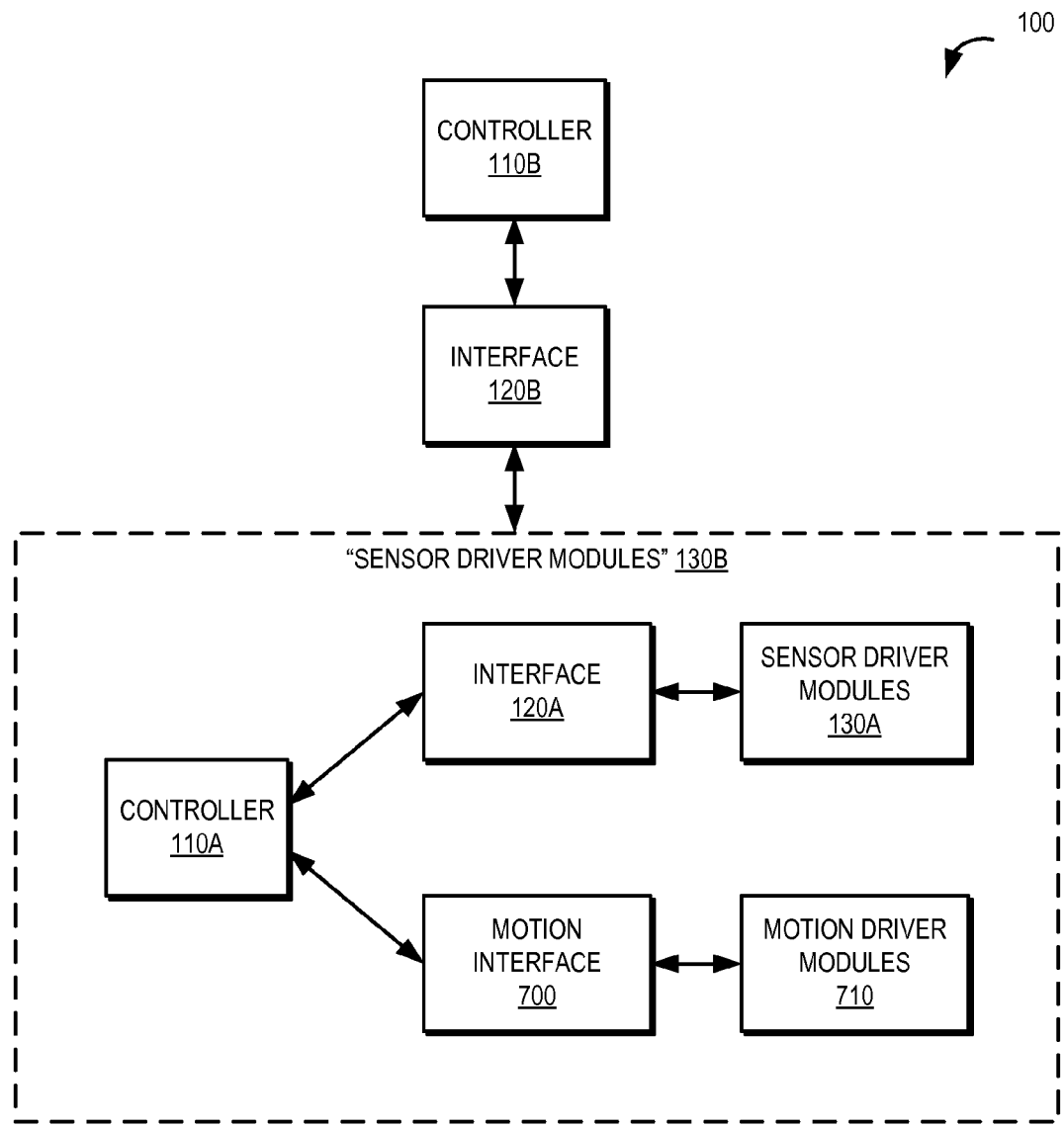
FIG. 7 illustrates a block diagram of a system for enabling a higher-level software application to query and control a composite sensor through a generic interface, according to another embodiment of the invention.

FIG. 7 illustrates a block diagram of a system for enabling a higher-level software application to query and control a composite sensor through a generic interface, according to another embodiment of the invention. The system 100 includes a controller 110B, an interface 120B, and a set of sensor driver modules 130B. The set of "sensor driver modules" 130B includes a controller 110A, an interface 120A, a set of sensor driver modules 130A, a motion interface 700, and a set of motion driver modules 710. The controller 110A, the interface 120A, and the set of sensor driver modules 130A shown in FIG. 7 are similar to the controller 110, the interface 120, and the set of sensor driver modules 130, respectively, shown in FIG. 1.

The motion interface 700 enables the controller 110A to control a motor via a set of motion driver modules 710, similar to how the interface 120A enables the controller 110A to query and control a sensor via a set of sensor driver modules 130A. The motion interface 700 and the set of motion driver modules 710 are further described in the following U.S. utility patent application, which is hereby incorporated by reference: Ser. No. 11/296,174, filed on Dec. 6, 2005, entitled "Interface for Robot Motion Control." In that patent application, the interface 120 represents the motion interface 700, and the set of robot driver modules 130 represents the set of motion driver modules 710.

Returning to FIG. 7 of the present application, the API of the interface 120B enables the controller 110B to issue commands for composite sensor data while shielding the controller 110B from the complexity of the set of sensor driver modules 130A and the set of motion driver modules 710. In this way, one controller 120B can issue a command for composite data, and the other controller 120A can generate the composite data by using the set of sensor driver modules 130A and the set of motion driver modules 710 and possibly performing additional computation. In this embodiment, the controller 110B queries and controls the composite sensor via the interface 120B and the set of "sensor driver modules" 130B.

Note that while FIGS. 4, 5, 6, and 7 described various systems 100 that included multiple controllers 110, multiple sets of sensor driver modules 130, a first type of composite sensor, and a second type of composite sensor, respectively, these systems can be combined to form additional types of systems. For example, an additional controller 110 can be added to the system 100 of FIG. 5 or the system 100 of FIG. 6. As another example, an additional set of sensor driver modules 130 can be added to the system 100 of FIG. 4 or the system 100 of FIG. 6.

Although the invention has been described in considerable detail with reference to certain embodiments thereof, other embodiments are possible as will be understood to those skilled in the art.

APPENDIX

ParameterRegistry["Kistler9286AA_Driver"]:
Parameter:
Id: 0
Name: "OperationState"
Comment: "Controls the operation state:
0=>reset,
1=>operating"
Valid ranges: "[0 . . . 1]"
Type: int
Units: "N/A"
Tunable: Yes
Lockable: Yes
OperationRegistrations:
OperationRegistration[
OperationID:OPERATION_SET
Signature: [R: int, A1: int]
]
OperationRegistration[
OperationID:OPERATION_READ
Signature: [R: int]
]
Parameter:
Id: 1
Name: "SamplingRate"
Comment: "Controls the driver sampling rate."
Valid ranges: "[50.0 . . . 500.0]"
Type: double
Units: "HZ"
Tunable: Yes
Lockable: Yes
OperationRegistrations:
OperationRegistration[
OperationID:OPERATION_SET
Signature: [R: double, A1: double]
]
OperationRegistration[
OperationID:OPERATION_READ
Signature: [R: double]
]
Parameter:
Id: 2
Name: "ShearForceSensitivity"
Comment: "Controls the force plate shear force sensitivity:
1=>−125.0 . . . +125.0 Newtons(N)
2=>−250.0 . . . +250.0 Newtons(N)
3=>−1250.0 . . . +1250.0 Newtons(N)
4=>−2500.0 . . . +2500.0 Newtons(N)"
Valid ranges: "[1 . . . 4]"
Type: int
Units: "N/A"
Tunable: Yes
Lockable: Yes
OperationRegistrations:
OperationRegistration[
OperationID:OPERATION_SET
Signature: [R: int, A1: int]
]
OperationRegistration[
OperationID:OPERATION_READ
Signature: [R: int]
]
Parameter:
Id: 3
Name: "VerticalForceSensitivity"
Comment: "Controls the force plate vertical force sensitivity:
1=>0.0 . . . +250.0 Newtons(N)
2=>0.0 . . . +500.0 Newtons(N)
3=>0.0 . . . +2500.0 Newtons(N)
4=>0.0 . . . +5000.0 Newtons(N)"
Valid ranges: "[1 . . . 4]"
Type: int
Units: "N/A"
Tunable: Yes
Lockable: Yes
OperationRegistrations:
OperationRegistration[
OperationID:OPERATION_SET
Signature: [R: int, A1: int]
]
OperationRegistration[
OperationID:OPERATION_READ
Signature: [R: int]
]
Parameter:
Id: 4
Name: "SensorAxisOffsets"
Comment: "Defines the sensor axis offsets:
[0]=SensorAxisOffset_z0, surface offset from x/y plane,

[1]=SensorAxisOffset_y, sensor axis offset from y-axis,
[2]=SensorAxisOffset_x, sensor axis offset from x-axis
"
Valid ranges: "N/A (constant values)"
Type: float[3]
Units: "m"
Tunable: No
Lockable: No
OperationRegistrations:
OperationRegistration[
OperationID:OPERATION_READ
Signature: [R: float[3]]
]
Parameter:
Id: 5
Name: "Output"
Comment: "
[0]=Fx12, Medio-Lateral force from force plate sensors 1 and 2 in Newtons(N),
[1]=Fx34, Medio-Lateral force from force plate sensors 3 and 4 in Newtons(N),
[2]=Fy14, Anterior-Posterior force from force plate sensors 1 and 4 in Newtons(N),
[3]=Fy23, Anterior-Posterior force from force plate sensors 2 and 3 in Newtons(N),
[4]=Fz1, Vertical force from force plate sensor 1 in Newtons(N),
[5]=Fz2, Vertical force from force plate sensor 2 in Newtons(N),
[6]=Fz3, Vertical force from force plate sensor 3 in Newtons(N),
[7]=Fz4, Vertical force from force plate sensor 4 in Newtons(N),
[8]=Fx, Total Medio-Lateral force (Fx12+Fx34) in Newtons(N),
[9]=Fy, Total Anterior-Posterior force (Fy14+Fy23) in Newtons(N),
[10]=Fz, Total Vertical force (Fz1+Fz2+Fz3+Fz4) in Newtons(N),
[11]=Ft, Resultant force (sqrt(Fx2+Fy2+Fz**2)) in Newtons(N),
[12]=Mx, Force plate moment about x-axis (SensorAxisOffset_x*(Fz1+Fz2−Fz3−Fz4)) in Newton-meters(Nm),
[13]=My, Force plate moment about y-axis (SensorAxisOffset_y*(Fz1+Fz2+Fz3−Fz4)) in Newton-meters(Nm),
[14]=Mx_top, Force plate moment about top plate surface [x-axis](Mx+Fy*SensorAxisOffset_z0) in Newton-meters (Nm),
[15]=My_top, Force plate moment about top plate surface [y-axis](My+Fx*SensorAxisOffset_z0) in Newton-meters (Nm),
[16]=Mz, Force plate moment about z-axis (SensorAxisOffset_x*(−Fx12+Fx34)+SensorAxisOffset_y*(Fy14−Fx23)) in Newton-meters(Nm),
[17]=COPx, Center of pressure x-coordinate (My_top/Fz) in Meters(m),
[18]=COPy, Center of pressure y-coordinate (Mx_top/Fz) in Meters(m),
[19]=Tz, Free moment Vertical Torque (Mz−Fy*COPx+Fx*COPy) in Newton-meters(Nm),
[20]=COFx, Coefficient of friction in x-direction (Fx/Fz),
[21]=COFy, Coefficient of friction in y-direction (Fy/Fz),
[22]=COFxy, Resultant coefficient of friction (sqrt (COFx2+COFy2))"
Valid ranges: "(See Parameter 2 and Parameter 3 above for Fxnn, Fynn, and Fznn ranges)"
Type: float[23]
Units: "(See units above)"
Tunable: No
Lockable: No
OperationRegistrations:
OperationRegistration[
OperationID:OPERATION_READ
Signature: [R: float[23]]
]

What is claimed is:

1. A method for controlling a composite sensor in a robot, wherein the composite sensor includes a plurality of sensors and a simple-sensor controller application that controls the plurality of sensors, the method comprising:
defining a parameter of the composite sensor, wherein the parameter describes a state of the composite sensor, wherein the simple-sensor controller application obtains simple sensed data from the plurality of sensors and processes the obtained data to generate composite data;
an interface module receiving, from a composite-sensor controller application, a software command that is sensor-independent of composite sensor commands and sensor-independent of sensor commands and an indication of the parameter;
the interface module determining a composite-sensor-dependent software command based on the composite-sensor-independent software command and the indication of the parameter;
the interface module sending, to the simple-sensor controller application, the composite-sensor-dependent software command; and
wherein the composite-sensor-independent software command includes a starting time that indicates when to execute the composite-sensor-independent software command.

2. The method of claim 1, wherein the parameter describes a configuration of the composite sensor.

3. The method of claim 1, wherein the parameter describes data sensed by the composite sensor.

4. The method of claim 1, wherein defining the parameter of the composite sensor comprises specifying whether a value of the parameter can be set.

5. The method of claim 1, wherein executing the composite-sensor-dependent software command sets a value of the parameter.

6. The method of claim 1, wherein executing the composite-sensor-dependent software command sets a default value of the parameter.

7. The method of claim 1, wherein executing the composite-sensor-dependent software command sets a value of the parameter to a default value.

8. The method of claim 1, wherein executing the composite-sensor-dependent software command sets a factory default value of the parameter.

9. The method of claim 1, wherein executing the composite-sensor-dependent software command sets a value of the parameter to a factory default value.

10. The method of claim 1, wherein executing the composite-sensor-dependent software command prevents a value of the parameter from being set.

11. The method of claim 1, wherein executing the composite-sensor-dependent software command allows a value of the parameter to be set.

12. The method of claim 1, wherein receiving, from the composite-sensor controller application, the composite-sensor-independent software command and the indication of the parameter comprises receiving, from one of a plurality of composite-sensor controller applications, the composite-sensor-independent software command and the indication of the parameter.

13. The method of claim 1, wherein receiving, from the composite-sensor controller application, the composite-sensor-independent software command and the indication of the parameter comprises receiving, from the composite-sensor controller application, a set of commands and parameter indications that includes the composite-sensor-independent software command and the indication of the parameter.

14. The method of claim 1, wherein sending, to the simple-sensor controller application, the composite-sensor-dependent software command comprises sending, to one of a plurality of simple-sensor controller applications, the composite-sensor-dependent software command.

15. The method of claim 1, further comprising:
receiving, from the simple-sensor controller application, a reply; and
sending, to the composite-sensor controller application, the reply.

16. The method of claim 15, wherein the reply includes a value of the parameter.

17. A system for controlling a composite sensor in a robot, wherein the composite sensor includes a plurality of sensors and a simple-sensor controller application that controls the plurality of sensors, the system comprising:
a processor;
means for defining a parameter of the composite sensor, wherein the parameter describes a state of the composite sensor, wherein the simple-sensor controller application obtains simple sensed data from the plurality of sensors and processes the obtained data to generate composite data;
means for receiving, from a composite-sensor controller application, a software command that is sensor-independent of composite sensor commands and sensor-independent of sensor commands and an indication of the parameter;
means for determining a composite-sensor-dependent software command based on the composite-sensor-independent software command and the indication of the parameter;
means for sending, to the simple-sensor controller application, the composite-sensor-dependent software command; and
wherein the composite-sensor-independent software command includes a starting time that indicates when to execute the composite-sensor-independent software command.

18. The system of claim 17, further comprising:
means for receiving, from the simple-sensor controller application, a reply; and
means for sending, to the composite-sensor controller application, the reply.

19. The system of claim 18, wherein the reply includes a value of the parameter.

* * * * *